United States Patent
Lentz

[11] Patent Number: 6,022,341
[45] Date of Patent: Feb. 8, 2000

[54] CATHETER WITH MULTIPLE INTERNAL DIAMETERS

[75] Inventor: David J. Lentz, LaJolla, Calif.

[73] Assignee: Medtronic, Inc., Minneapolis, Minn.

[21] Appl. No.: 08/943,473

[22] Filed: Oct. 3, 1997

[51] Int. Cl.[7] .................................................. A61M 25/00
[52] U.S. Cl. ........................................ 604/523; 604/264
[58] Field of Search .............................. 604/264, 93, 523, 604/524, 525, 532

[56] References Cited

U.S. PATENT DOCUMENTS

| | | |
|---|---|---|
| 4,563,180 | 1/1986 | Jervis et al. . |
| 5,533,988 | 7/1996 | Dickerson et al. ...................... 604/523 |
| 5,549,551 | 8/1996 | Peacock, III et al. ..................... 604/96 |
| 5,820,610 | 10/1998 | Baudino .................................. 604/523 |

FOREIGN PATENT DOCUMENTS

| | | |
|---|---|---|
| 0385920 | 9/1990 | European Pat. Off. . |
| 9104763 | 4/1991 | WIPO . |
| 9117782 | 11/1991 | WIPO . |
| 9714466 | 4/1997 | WIPO .......................... A61M 25/100 |

*Primary Examiner*—Ronald K. Stright, Jr.

[57] ABSTRACT

There is disclosed a medical catheter comprising a proximal shaft section and a distal shaft section. The proximal shaft section has an inner diameter and wall thickness which is constant over the length of the proximal shaft section. The distal shaft section has an inner diameter which is greater than the proximal shaft inner diameter and has a step up or taper therebetween. The proximal end of the distal shaft section is aligned proximal to the proximal end of a curved portion of the guiding catheter's distal shaft section.

8 Claims, 3 Drawing Sheets

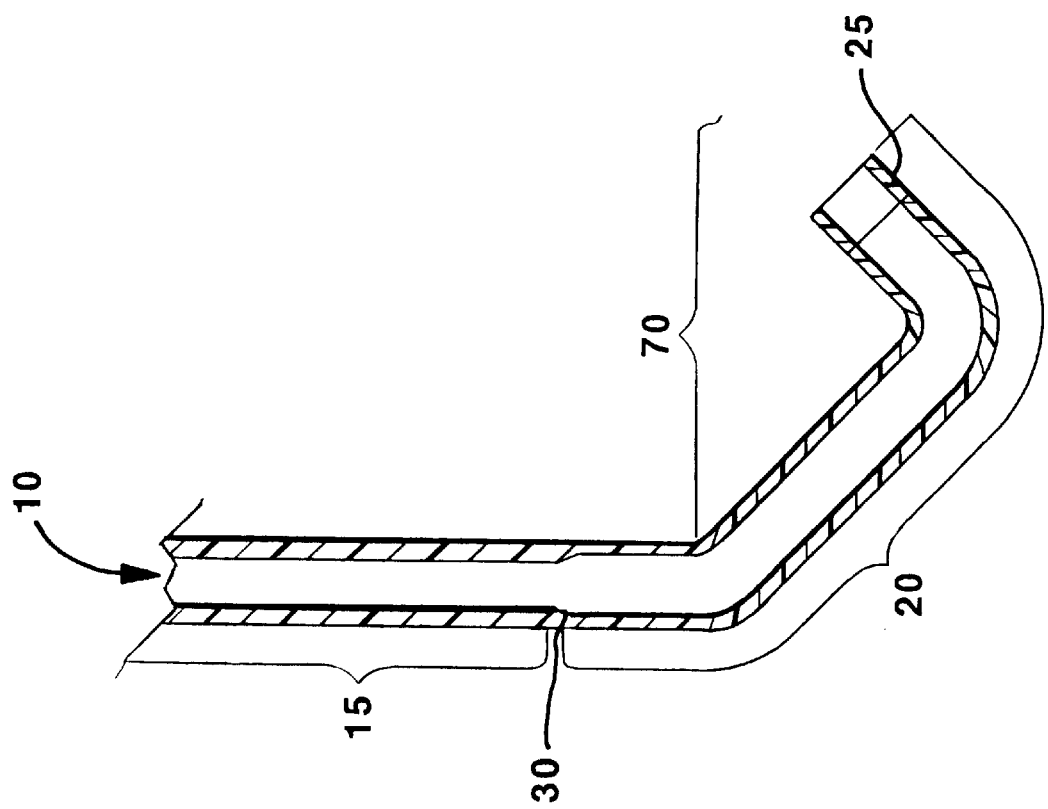

CATHETER WITH MULTIPLE INTERNAL DIAMETERS

FIELD OF THE INVENTION

The present invention relates to the field of catheters and more particularly to a guiding catheter for use in passing larger interventional devices.

BACKGROUND OF THE INVENTION

Percutaneous transluminal coronary angioplasty (PTCA) is used to increase the lumen diameter of a coronary artery partially or totally obstructed by a build-up of cholesterol fats or atherosclerotic plaque. Typically a first guidewire of about 0.038 inches in diameter is steered through the vascular system to the site of therapy. A guiding catheter, for example, can then be advanced over the first guidewire to a point just proximal of the stenosis. The first guidewire is then removed. A balloon catheter on a smaller 0.014 inch diameter second guidewire is advanced within the guiding catheter to a point just proximal of the stenosis. The second guidewire is advanced into the stenosis, followed by the balloon on the distal end of the catheter. The balloon is inflated causing the site of the stenosis to widen. The dilatation of the occlusion, however, can form flaps, fissures and dissections which threaten reclosure of the dilated vessel or even perforations in the vessel wall.

Although the dimensions in the above example are suited to the coronary arteries, any body lumen can be treated by percutaneous transluminal angioplasty (PTA), including the vas deferens, ducts of the gallbladder, prostate gland, trachea, bronchus and liver or larger arteries such as the renal and carotid. The body lumens range in diameter from small coronary vessels of 3 mm or less to 28 mm in the aortic vessel. The invention applies to acute and chronic closure or reclosure of body lumens.

Guiding catheters are used to pass larger interventional devices which are passed through guiding catheters such as balloon catheters, balloon catheters with a stent crimped thereon, laser devices or atherectomy devices. The distal end of a guiding catheter is typically preformed into a curve specifically designed to conform to the vasculature of the target site as for example, the Amplatz or Judkins curves. Larger interventional devices typically have an enlarged distal working end. Friction builds up in the curve of a guiding catheter when large interventional devices are passed through the guiding catheter curve.

After deployment, the interventional device is withdrawn into the guiding catheter for removal. Die injection flow through the guiding catheter is restricted when such large interventional devices are retracted into the guiding catheter. The interventional device can also snag on the distal end of the guiding catheter when withdrawn into the guiding catheter.

Prior art catheters typically have a shaft with an inner diameter and outer diameter which remain constant along the length of the shaft as seen in commonly owned, copending U.S. Ser. No. 08/543,992 (WO 97/14466) to Brin et al. for a "Guide Catheter with Soft Distal Segment" which discloses a guiding catheter with a flexural stiffness gradation along the length of the catheter.

Commonly owned U. S. Pat. No. 4,563,180 to Jervis et al. for "High Flow Catheter for Injecting Fluids" discloses a catheter with an inside diameter which varies over its length from a minimum at the proximal end to a maximum at the distal end. It is not necessary that the transition from the minimum inside diameter to the maximum inside diameter occur gradually and uniformly. However, it is particularly preferred that the inside diameter tapers toward the proximal end of the catheter.

It is an object of the invention to optimize the design of a catheter for delivering large interventional devices through guiding catheters which minimizes friction build-up in the curved area of the guiding catheter while maximizing fluid flow. It is a further object of the invention to reduce the possibility of interventional devices snagging on the distal end of the guiding catheter when the interventional device is withdrawn into the guiding catheter.

SUMMARY OF THE INVENTION

The present invention is accomplished by providing a guiding catheter for passing interventional devices comprising a proximal shaft section and a distal shaft section. The proximal shaft section has an inner diameter and wall thickness which is constant over the length of the proximal shaft section. The distal shaft section has an inner diameter which is greater than the proximal shaft section inner diameter with a step up or taper therebetween. The proximal end of the distal shaft section is aligned proximal to the proximal end of a curved portion of the guiding catheter's distal shaft section.

BRIEF DESCRIPTION OF THE DRAWINGS

FIG. 3 is the invention of FIG. 1 with a curved guiding catheter.

DETAILED DESCRIPTION OF THE PREFERRED EMBODIMENTS

Figure 1:
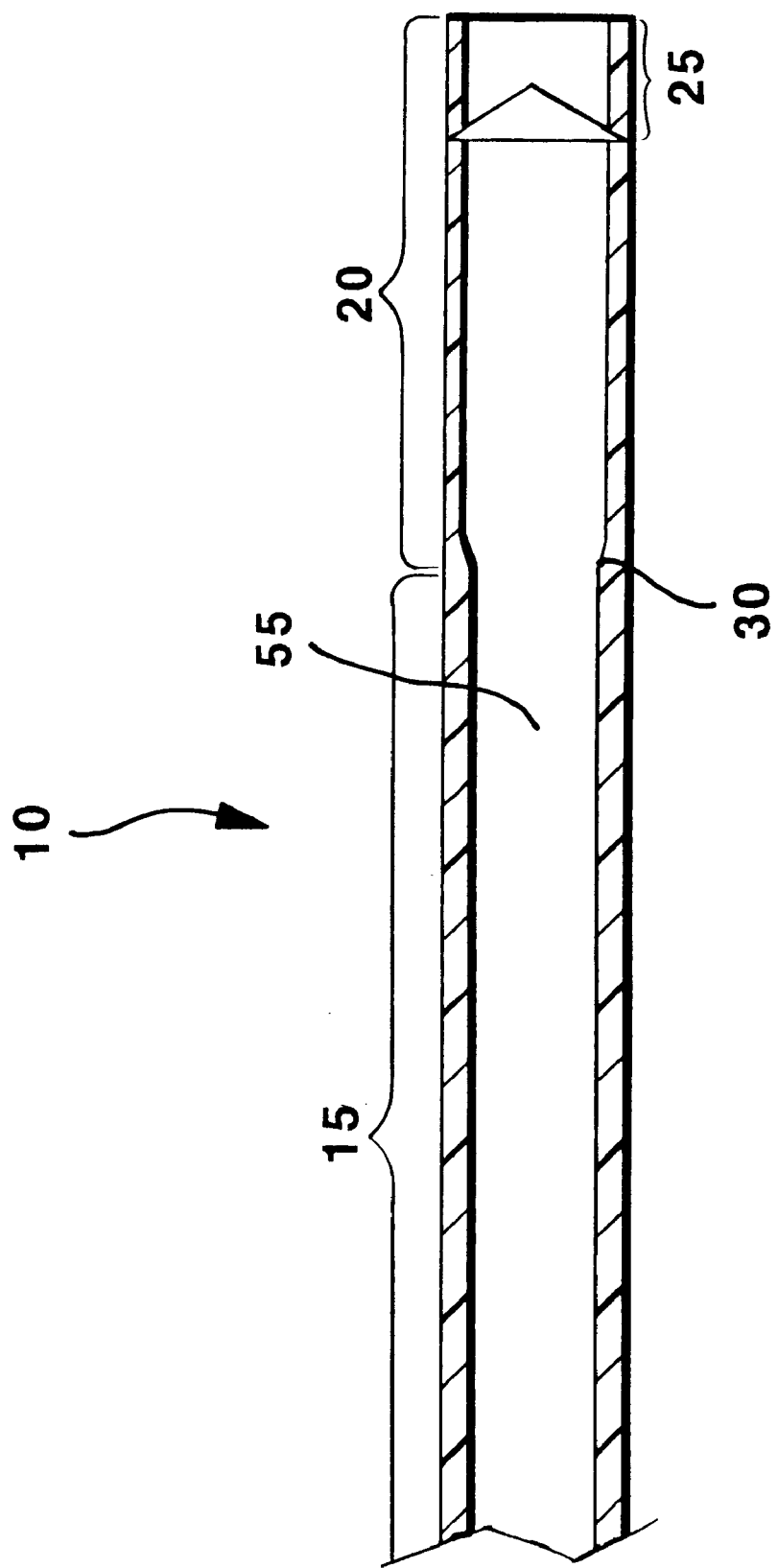
FIG. 1 is a transverse cross-section of the guiding catheter of the invention.

Referring to FIG. 1, which discloses a guiding catheter 10 for delivering large interventional devices. The guiding catheter 10 has a proximal shaft section 15, a distal shaft section 20 and an optional soft tip section 25. The inner diameter of the proximal shaft section 15 is less than the inner diameter of the distal shaft section 20. The soft tip section 25 is formed at the distal end of the distal shaft section 20. The soft tip 25 may be constructed by variety of methods as for example, that of commonly owned, copending U.S. Ser. No. 08/543,992 (WO 97/14466) to Brin et al. for a "Guide Catheter with Soft Distal Segment" which is hereby incorporated by reference.

As seen in FIG. 3, the inner diameter of the proximal shaft section 15 is constant and becomes greater in the distal shaft section 20 generally proximal to, and preferably just proximal to, the point where the guiding catheter begins to form a curved portion 70. Thus, the step up or taper 30 is aligned just proximal to the proximal end of the guiding catheter 10 curved portion 70 found in the distal shaft section 20. The enlarged distal shaft section lumen results in less friction when large interventional devices are passed through the curved portion 70 of the guiding catheter 10 corresponding to the distal shaft section 20.

Figure 2:
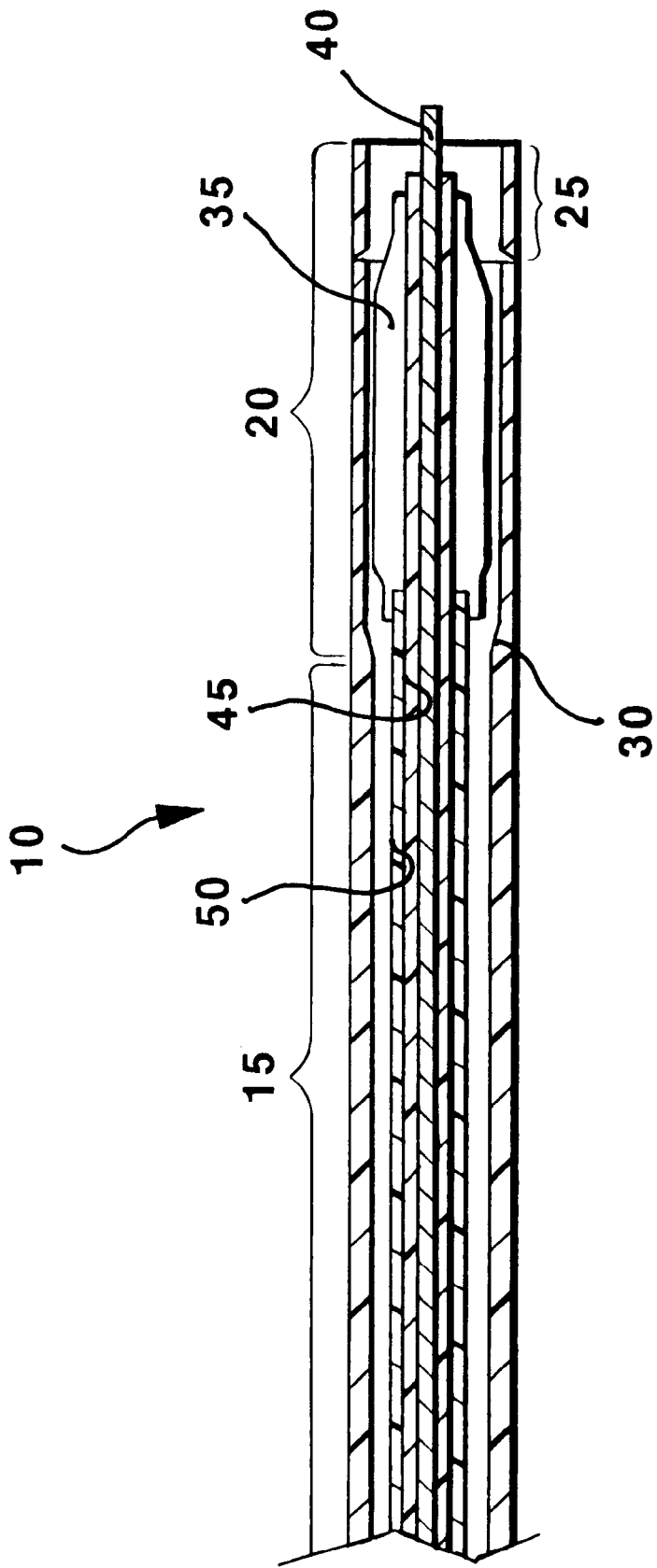
FIG. 2 is the invention of FIG. 1 with a balloon catheter and guidewire therein.

Another advantage of applicant's invention is that it also permits greater injected die flow due to increased clearance when the enlarged distal working end of the interventional device such as a balloon 35 is retracted into the guiding catheter 10. Refer to FIG. 2 showing an over-the-wire balloon catheter within the guiding catheter 10. Other types of balloon catheters could be used, such as rapid exchange or fixed wire balloon catheters. The standard over-the-wire balloon catheter is advanced over a guidewire 40 running through the guide wire lumen 45 to the lesion. The balloon 35 is inflated through the inflation lumen 50. The balloon 35 is withdrawn into the guide catheter 10. Die is injected to visualize the widened lesion. Because the distal shaft section 20 has been enlarged, greater die flow is possible around the balloon 35 when the balloon 35 is retracted into the distal shaft section 20, thereby permitting greater visualization of the lesion for more precise determination of therapeutic affect.

A further advantage of applicant's invention is that the enlarged inner diameter of the distal shaft section 20 enables devices to be retracted into the guiding catheter 10 without catching on the distal end of the guiding catheter 10 while reducing the retraction force when entering the distal end of the guiding catheter 10. This is especially important for devices such a stent delivery system including a balloon catheter with a stent crimped thereon should the delivery system need to be retracted before deployment for any reason.

A guiding catheter 10 according to the invention could be of any French size. Preferred sizes for coronary applications are 5F to 10F. Given the Vector™ guiding catheter construction disclosed in Brin et al. supra, with a braided wire reinforcement, wall thickness is sufficient for about a 0.004 inches inch maximum step up or taper 30. Those skilled in the art would recognize that other designs and technologies may permit a step up or taper of different sizes. The step up or taper 30 provides a smooth transition between the proximal shaft section 15 and the distal shaft section 20. The length of the step up or taper 30 should be gradual and smooth to minimize snagging of the interventional devices being passed through the guiding catheter 10.

Whereas the larger internal diameter is beneficial for the distal shaft section 20, it is not necessary for the proximal shaft section 15. Retaining the smaller internal diameter for the proximal shaft section 15 retains the benefits of the structural properties of greater wall thickness. These benefits include better torque control as well as better longitudinal and rotational or translational kink resistance. Greater wall thickness in the proximal shaft section 15 also provides greater backup support enabling the catheter to sustain itself better in the artery. Because of the benefits of greater wall thickness it is advantageous to maintain a constant inner diameter throughout the proximal shaft section 15.

If a 10F guiding catheter is used the following approximate dimensions apply. A standard 10 French guiding catheter has an outer diameter of 3.3 mm or 0.131 inches. For a 10 French Vector™ guiding catheter the step up or taper 30 could range from 0.002 inches to 0.004 inches. There is insufficient wall thickness in a 10 French Vector™ guiding catheter for a step up or taper 30 greater than 0.004 inches. Accordingly, if the inner diameter of the proximal shaft section 15 is 0.110 inches, the step up or taper could range from 0.002 inches to 0.006 inches yielding a distal shaft section 20 with an inner diameter of 0.112 to 0.116 inches. If the inner diameter of the proximal shaft section is 0.112 inches, the step up or taper 30 could range from 0.002 inches to 0.004 inches yielding a distal shaft section 20 with an inner diameter of 0.114 inches to 0.116 inches.

For interventional devices such as coronary balloon catheters, a 9 French guiding catheter may be advantageous. A standard 9 French guiding catheter has an outer diameter of 3.0 mm or 0.118 inches. For a 9 French Vector™ guiding catheter, the step up or taper 30 could range from approximately 0.002 inches to 0.004 inches. There is insufficient wall thickness in a 9 French Vector™ guiding catheter for a step up or taper 30 greater than approximately 0.004 inches. Accordingly, if the inner diameter of the proximal shaft section 15 is 0.100 inches, the step up or taper 30 would range from approximately 0.002 inches to 0.004 inches yielding a distal shaft section 20 with an inner diameter ranging from 0.102 inches to 0.104 inches. If the inner diameter of the proximal shaft section is 0.102 inches, the step up or taper would be approximately 0.002 inches yielding a distal shaft section 20 with an inner diameter of 0.104 inches.

If an 8F guiding catheter is used the following approximate dimensions apply. A standard 8French guiding catheter has an outer diameter of 2.7 mm or 0.105 inches. For an 8 French Vector™ guiding catheter the step up or taper 30 could range from 0.002 inches to 0.004 inches. There is insufficient wall thickness in a 8 French Vector™ guiding catheter for a step up or taper 30 greater than 0.004 inches. Accordingly, if the inner diameter of the proximal shaft section 15 is 0.086 inches, the step up or taper 30 could range from 0.002 inches to 0.004 inches yielding a distal shaft section 20 with an inner diameter of 0.088 to 0.090 inches. If the inner diameter of the proximal shaft section is 0.088 inches, the step up or taper 30 could be 0.002 inches yielding a distal shaft section 20 with an inner diameter of 0.090 inches.

If an 7F guiding catheter is used the following approximate dimensions apply. A standard 7 French guiding catheter has an outer diameter of 2.3 mm or 0.092 inches. For a 7 French Vector™ guiding catheter the step up or taper 30 could range from 0.002 inches to 0.004 inches. There is insufficient wall thickness in a 7 French Vector™ guiding catheter for a step up or taper 30 greater than 0.004 inches. Accordingly, if the inner diameter of the proximal shaft section 15 is 0.074 inches, the step up or taper 30 could range from 0.002 inches to 0.004 inches yielding a distal shaft section 20 with an inner diameter of 0.076 to 0.078 inches. If the inner diameter of the proximal shaft section is 0.076 inches, the step up or taper 30 could be 0.002 inches yielding a distal shaft section 20 with an inner diameter of 0.078 inches.

If a 6F guiding catheter is used the following approximate dimensions apply. A standard 6 French guiding catheter has an outer diameter of 2.0 mm or 0.081 inches. For a 6 French Vector™ guiding catheter the step up or taper 30 could range from 0.002 inches to 0.004 inches. There is insufficient wall thickness in a 6 French Vector™ guiding catheter for a step up or taper 30 greater than 0.004 inches. Accordingly, if the inner diameter of the proximal shaft section 15 is 0.064 inches, the step up or taper 30 could range from 0.002 inches to 0.004 inches yielding a distal shaft section 20 with an inner diameter of 0.066 to 0.068 inches. If the inner diameter of the proximal shaft section is 0.066 inches, the step up or taper 30 could be 0.002 inches yielding a distal shaft section 20 with an inner diameter of 0.068 inches.

If a 5F guiding catheter is used the following approximate dimensions apply. A 5 French guiding catheter may have an outer diameter range of 0.065 inches to 0.068 inches. For a 5French Vector™ guiding catheter the step up or taper 30 could range from 0.002 inches to 0.004 inches with an inner diameter ranging from 0.054 inches to 0.060 inches. Accordingly, if the inner diameter of the proximal shaft section 15 is 0.054 inches, the step up or taper 30 could range from 0.002 inches to 0.004 yielding a distal shaft section 20 with an inner diameter of 0.056 to 0.058 inches.

If the inner diameter of the proximal shaft section is 0.056 inches, the step up or taper 30 could range from 0.002 inches to 0.004 inches yielding a distal shaft section 20 with an inner diameter of 0.058 inches to 0.060 inches. If the inner diameter of the proximal shaft section is 0.058 inches, the step up or taper 30 could range from 0.002 inches to 0.004 inches yielding a distal shaft section 20 with an inner diameter of 0.060 inches to 0.062 inches. If the inner diameter of the proximal shaft section is 0.060 inches, the step up or taper 30 could be 0.002 inches yielding a distal shaft section 20 with an inner diameter of 0.062 inches. A guiding catheter 10 could be manufactured using a variety of different materials using various methods recognized by those skilled in the art. A guiding catheter 10 could be made, for example according to the method of this invention as follows. A thin polymer liner measuring approximately 0.002 to 0.003 inches in thickness is extruded over a core material. The core is removed later in the manufacturing process. The core material is selected to have a higher melt temperature than the liner, thus preventing bonding between the two during processing. The core outer diameter is identical to that of the desired guide catheter lumen 55 dimension. Flat or round wire is braided over the core and liner in any suitable manner to form the braided tube. The braid is formed from a stiff metal, 304 stainless steel ranging in temper from annealed to double spring temper, having a width from 0.003 to 0.015 inches and a thickness from 0.0007 to 0.0015 inches. The braid is a 2 over 2 pattern ranging in pic count from 30 to 70 pics per inch. The polymer outer jacket is extruded over the braided tube. The outer jacket application process promotes bonding between the outer jacket material and the inner liner, thus encapsulating the braid pattern.

The proximal shaft section 15 of a smaller lumen size is joined to a larger lumen distal shaft section 20 through a thermal welding process such as radio frequency welding, a melt bonding process which results in a gradual and smooth inner diameter transition between the proximal shaft section 15 and the distal shaft section 20. The length of the step up or taper 30 transition between the proximal shaft section 15 and the distal shaft section 20 is between 0.002 inches and 0.25 inches. The gradual step up or taper 30 transition will minimize devices snagging thereon when passed through the guiding catheter step up or taper 30. Other means of affixing the proximal shaft section 15 to the distal shaft section 20 such as shrink wrapping are unsatisfactory because the subtle 0.002 inch to 0.004 inch step up or taper 30 would not be retained under the forces of shrink wrapping without the need of adding manufacturing steps involving the use of a stepped mandrel.

A softer, more flexible material is attached to the distal end of the catheter forming a soft tip section 25. Catheter materials are selected so that the shaft and distal segments may be shaped into a variety of curve 70 styles to conform to a wide variety of anatomies. A ANSI standard Luer hub is manufactured from a polymer, such as ABS, and attached to the proximal shaft with an adequate strain relief using an engineering adhesive. A lubricant is coated onto the internal guide catheter surface in order to allow interventional devices to be inserted and removed using less force.

The preceding specific embodiments are illustrative of the practice of the invention. It is to be understood, however, that other expedients known to those skilled in the art or disclosed herein, may be employed without departing from the scope of the appended claims.

What is claimed is:

1. A medical catheter comprising:

a proximal shaft section having an inner diameter, outer diameter and a wall thickness, the inner diameter being constant over the length of the proximal shaft section, the wall thickness being constant over the length of the proximal shaft;

a distal shaft section having an inner diameter, outer diameter and a wall thickness, the distal shaft section inner diameter being greater than the proximal shaft section inner diameter, the distal end of the proximal shaft section being connected to the proximal end of the distal shaft section by a step up and wherein a proximal end of the distal shaft section is aligned proximal to the proximal end of a curved portion of the distal shaft section.

2. The catheter according to claim 1 wherein the step up is a taper which forms a smooth and gradual transition between the inner diameter of the proximal shaft section and the inner diameter of the distal shaft section.

3. The catheter according to claim 2 wherein the taper is formed by thermal welding.

4. The catheter according to claim 1 wherein the distal shaft section inner diameter is sized to slidingly receive interventional devices.

5. The catheter according to claim 1 wherein the inner diameter of the distal shaft section is 0.002 inches to 0.004 inches larger than the inner diameter of the proximal shaft section.

6. The catheter according to claim 1 wherein the inner diameter of the distal shaft section remains constant over the length of the distal shaft section.

7. The catheter according to claim 1 wherein the wall thickness of the distal shaft section remains constant over the length of the distal shaft section.

8. The catheter according to claim 1 wherein the outer diameter of the proximal shaft section is equal to the outer diameter of the distal shaft section.

* * * * *